(12) United States Patent
Piantoni et al.

(10) Patent No.: US 10,470,938 B2
(45) Date of Patent: Nov. 12, 2019

(54) PROCESS FOR FORMING ABSORBENT SANITARY ARTICLES

(71) Applicant: GDM S.p.A., Bologna (IT)

(72) Inventors: Matteo Piantoni, Albina (IT); Valerio Soli, Bologna (IT)

(73) Assignee: GDM S.P.A., Bologna (IT)

( * ) Notice: Subject to any disclaimer, the term of this patent is extended or adjusted under 35 U.S.C. 154(b) by 0 days.

(21) Appl. No.: 15/517,815

(22) PCT Filed: Sep. 21, 2015

(86) PCT No.: PCT/IB2015/057252
§ 371 (c)(1),
(2) Date: Apr. 7, 2017

(87) PCT Pub. No.: WO2016/055885
PCT Pub. Date: Apr. 14, 2016

(65) Prior Publication Data
US 2017/0326005 A1    Nov. 16, 2017

(30) Foreign Application Priority Data
Oct. 10, 2014    (IT) .............................. BO2014A0552

(51) Int. Cl.
*A61F 13/15*    (2006.01)

(52) U.S. Cl.
CPC .. *A61F 13/15723* (2013.01); *A61F 13/15577* (2013.01); *A61F 2013/15821* (2013.01)

(58) Field of Classification Search
CPC .......... A61F 13/15723; A61F 13/15577; A61F 13/15756; A61F 13/56; A61F 13/49009; A61F 2013/15821
See application file for complete search history.

(56) References Cited

U.S. PATENT DOCUMENTS

| | | |
|---|---|---|
| 2008/0161766 A1 | 7/2008 | Sablone et al. |
| 2011/0100536 A1 | 5/2011 | Umebayashi |
| 2011/0146902 A1 | 6/2011 | Wada et al. |

FOREIGN PATENT DOCUMENTS

| | | |
|---|---|---|
| EP | 1941853 A1 | 7/2008 |
| EP | 2238955 A1 | 10/2010 |

(Continued)

OTHER PUBLICATIONS

International Search Report dated Dec. 7, 2015 from counterpart PCT App No. PCT/IB2015/057252.

(Continued)

*Primary Examiner* — Mark A Osele
*Assistant Examiner* — Christopher C Caillouet
(74) *Attorney, Agent, or Firm* — Shuttleworth & Ingersoll, PLC; Timothy J. Klima

(57) ABSTRACT

A process for forming an absorbent sanitary article includes feeding a first web including first and second stretches each having front and rear end portions; feeding a second web for forming a first side panel of the article; feeding a third web for forming a second side panel of the article; cutting the second web into a succession of first and second pieces defining the first side panel of the article; cutting the third web in a succession of third and fourth pieces, defining the second side panel of the article; applying the first through fourth pieces to the first web; the first and second stretches being provided in the first web so each first stretch has the rear end portion upstream of the front end portion in a feed direction and each second stretch has the front end portion upstream of the rear end portion.

20 Claims, 4 Drawing Sheets

(56) References Cited

FOREIGN PATENT DOCUMENTS

| | | | |
|---|---|---|---|
| EP | 2586411 | A1 | 5/2013 |
| JP | H04261655 | A | 9/1992 |
| JP | 2010514485 | A | 5/2010 |
| JP | 2010119423 | A | 6/2010 |
| JP | 2011025079 | A | 2/2011 |
| WO | 2010032396 | A1 | 2/2012 |

OTHER PUBLICATIONS

Japanese Office Action dated May 24, 2019 for counterpart Japanese Patent Application No. 2017-518823.

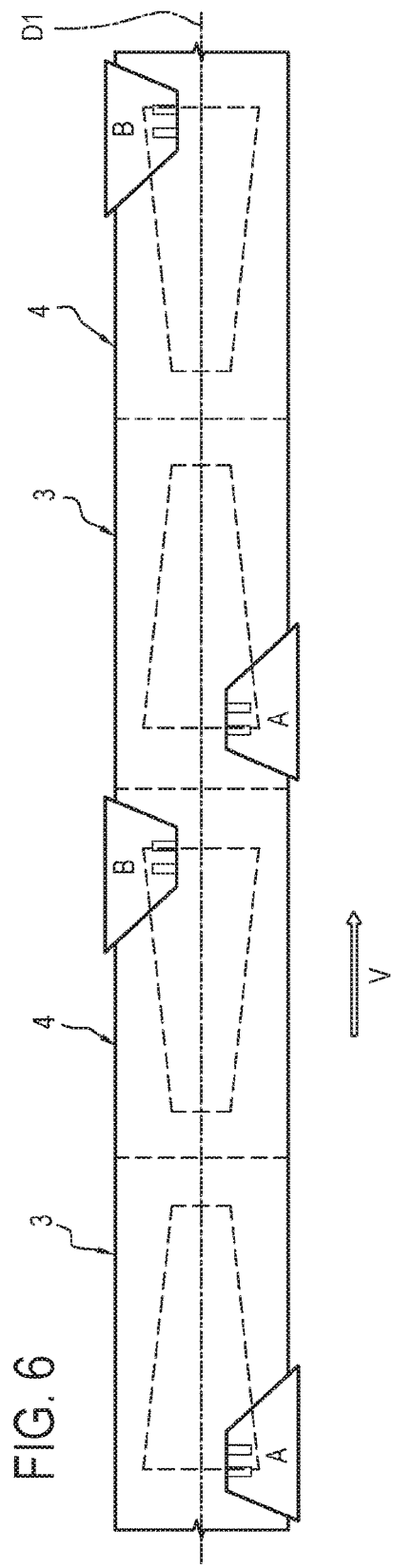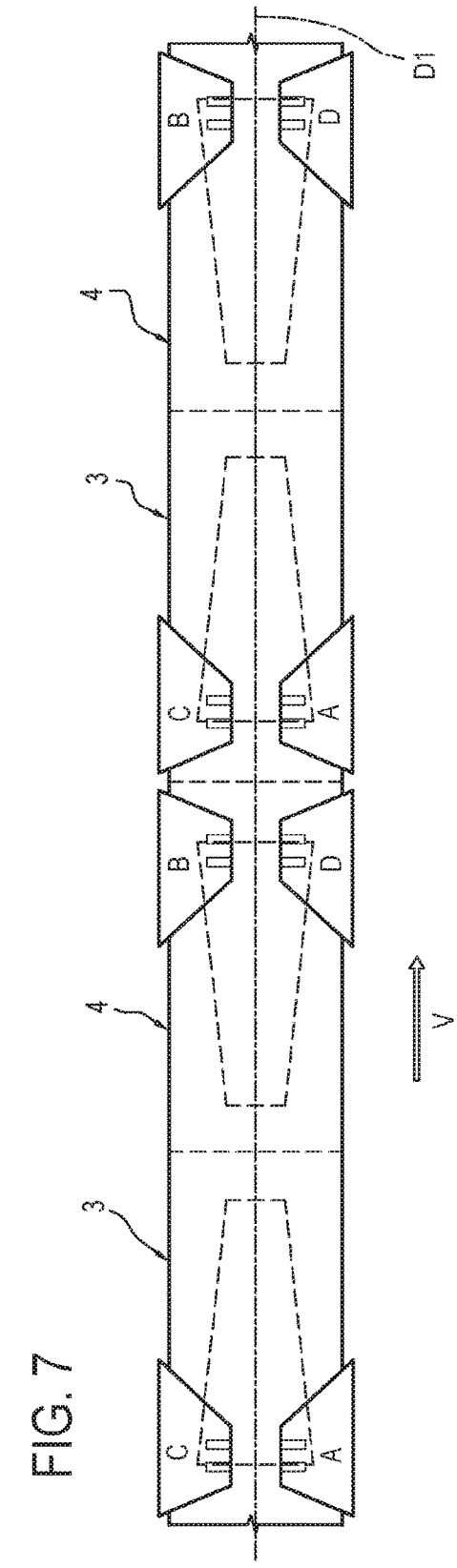

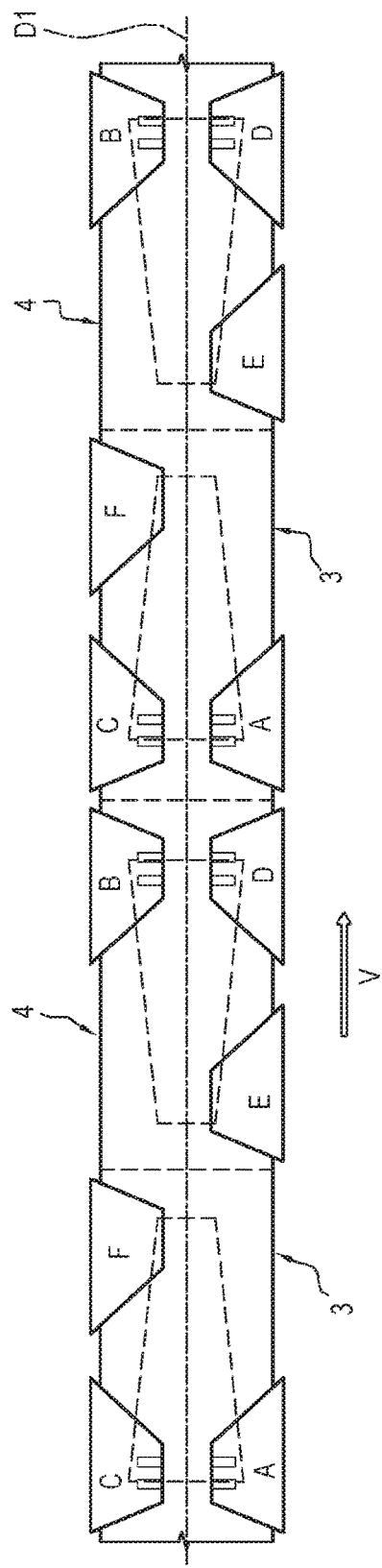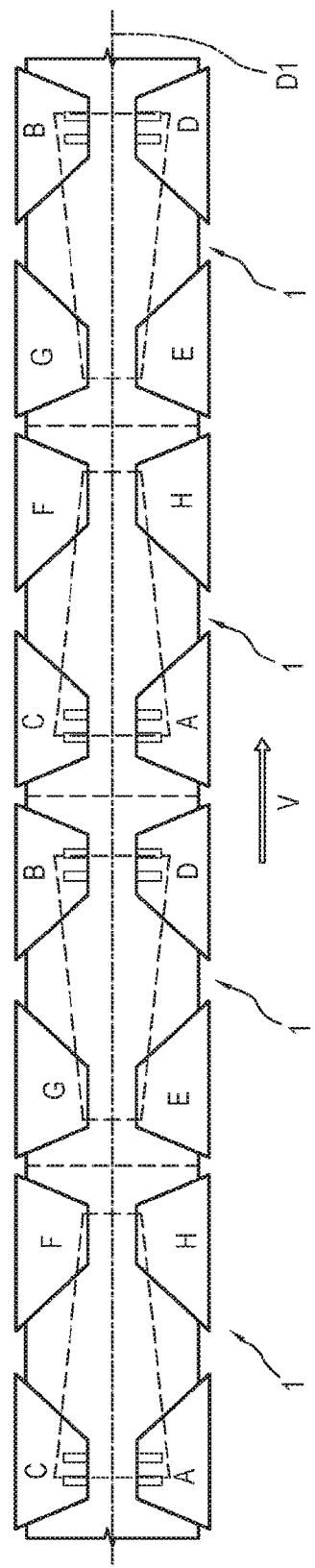
FIG. 8
FIG. 9

PROCESS FOR FORMING ABSORBENT SANITARY ARTICLES

This application is the National Phase of International Application PCT/IB2015/057252 filed Sep. 21, 2015 which designated the U.S.

This application claims priority to Italian Patent Application No. BO2014A000552 filed Oct. 10, 2014, which application is incorporated by reference herein.

TECHNICAL FIELD

This invention relates to a process for forming absorbent sanitary articles such as nappies for babies to which reference is hereinafter made without limiting the scope of the invention.

BACKGROUND ART

There are prior art absorbent sanitary articles comprising a main body, defined in general as a piece of a composite web and having a main direction of extension.

The main body has a front end portion, known to experts in the field simply as "front", designed to be positioned, in use, in front of a user, and a rear end portion, known to experts in the field simply as "back" designed to be positioned, in use, behind the user.

The absorbent articles of known type comprise a pair of side panels or flaps, possibly comprising more parts connected to each other, which extend on opposite sides of the front end portion, in the jargon of the trade known as "front panel", and a pair of side panels or flaps, possibly comprising more parts connected to each other, which extend on opposite sides of the rear end portion, in the jargon of the trade known as "back panel".

The rear panels are generally provided with systems for attaching or joining to the corresponding front panel, if present, to encircle the waist of the user.

As is known, both the front panels and the rear panels are made, during the manufacture of the nappies, from webs which are cut into pieces and then connected to the main body or, more generally, during the assembly, on a layer of the composite web which will constitute the main body, feeding along a feed path.

The front or rear panels have, in general, two sides which are parallel to one another, one of which being designed to connect with the main body and the opposite one designed to engage with the corresponding rear or front panel when the nappy is worn.

In general, due to reasons of cost and wearability and convenience of the nappy, the front and rear panels are made of materials and with shapes which are different from each other and, therefore, the processes for forming the front and rear panels are generally different from each other.

Wearability requirements have led to the development of so-called "asymmetrical" panels, that is, for example, in the shape of trapezium, in particular scalene, wherein the bases comprise the above-mentioned parallel sides.

Another important requirement in these processes is to attempt not to have waste material, that is, to use all the material of the webs to obtain panels; the processes for making panels without waste material are known in the sector as "zero waste" processes.

The cutting of the webs for forming the panels in trapezoidal shapes, without waste material, generally implies that, for each web, there are panels which are correctly oriented, with reference to the position of application on the main body, and others which are not.

To overcome the above mentioned drawback, processes have been developed which comprise, in short, the rotation of those panels which are not correctly positioned or oriented relative to the web on which they must be applied. Examples of these solutions are described in patent documents EP1941853 and EP2238955.

The processes which comprise the rotation of the panels before the application to the main body have some drawbacks.

The devices which actuate these rotations are complex and expensive.

The rotation of the panels has critical aspects at the high speeds during formation of the nappies.

DISCLOSURE OF THE INVENTION

In this context, the main purpose of this invention is to provide a process for forming absorbent sanitary articles which overcomes the above-mentioned drawbacks.

One aim of this invention is to provide a process for forming absorbent sanitary articles which allows nappies to be made with side panels or flaps with different shapes and/or materials between the front and rear.

Another aim of this invention is to provide a process for forming absorbent sanitary articles which is of the so-called "zero waste" type.

The technical purpose and aims specified are substantially achieved by a process for forming absorbent sanitary articles comprising technical features as disclosed herein.

BRIEF DESCRIPTION OF DRAWINGS

Further features and advantages of this invention are more apparent in the detailed description below, with reference to a preferred, non-limiting embodiment of a process for forming absorbent sanitary articles as illustrated in the accompanying drawings, in which:

FIGS. 1 to 9 illustrate a schematic plan view of a schematic sequence of steps of the process for forming absorbent articles according to this invention.

DETAILED DESCRIPTION OF PREFERRED EMBODIMENTS OF THE INVENTION

With reference to the accompanying drawings, in particular with reference to FIG. 9, the numeral 1 denotes a semi-finished item designed to become an absorbent sanitary article or nappy to which reference is hereinafter made without limiting the scope of the invention.

The semi-finished items are 1 linked together in a continuous succession defined by a composite web comprising at least one layer.

The generic absorbent sanitary article comprises a main body, of substantially known type, generally comprising a plurality of layers, for example a topsheet, a backsheet and an absorbent pad interposed between the backsheet and the topsheet.

The main body has a main direction of extension and a front end portion designed to be positioned, in use, in front of the user, and a rear end portion designed to be positioned, in use, behind the user, the nappy being folded in a "U" shape around the crotch of the user.

The absorbent article is generally equipped with a first and a second front panel or flap, with reference to the nappy worn by the user, extending laterally from the front end portion and a first and a second rear panel or flap, with reference to the nappy worn by the user, extending laterally from the rear end portion.

The front and rear panels are fitted out, in known manner, to engage with each other, encircle the waist of the generic user and keep the nappy, in use, in a correct position.

Figure 1:
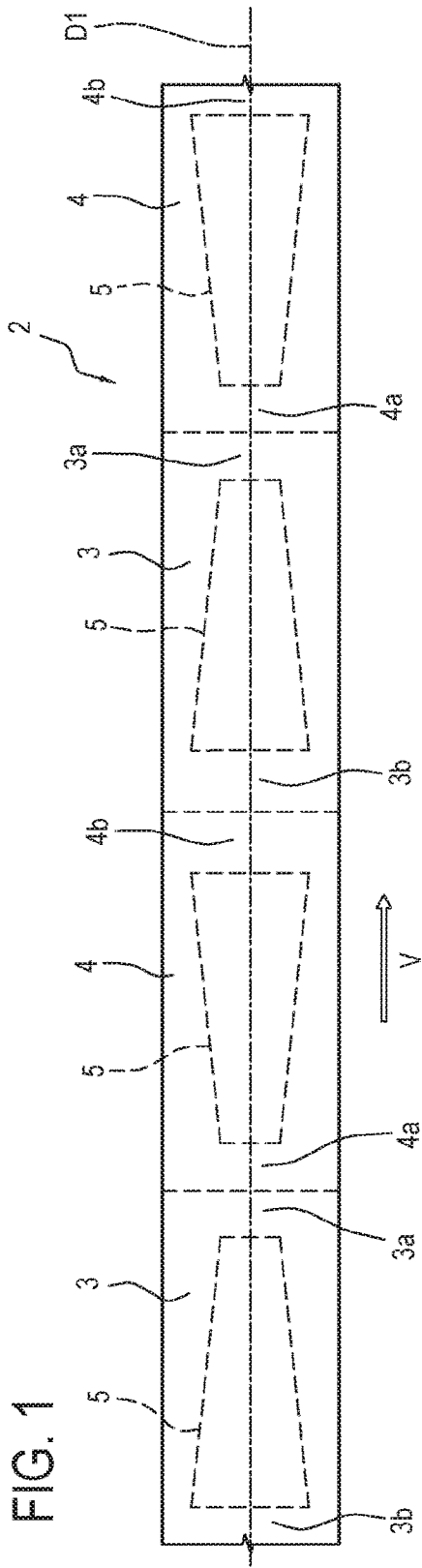

With reference to FIG. 1, the process for making an absorbent article comprises a step of feeding, in a feed direction V, a first web 2 comprising first and second stretches 3, 4, each designed to define at least a first layer of the main body of the absorbent article.

The stretches 3, 4 of the web 2 each comprise a front end portion 3a, 4a and a rear end portion 3b, 4b corresponding to the front end portion and the rear end portion of the corresponding main body of the absorbent article.

In other words, the ends 3a, 4a and 3b, 4b are defined, respectively, as front and rear once the absorbent sanitary article has been finished.

The web 2 has a main direction of extension D, coinciding with the main direction of extension of the main body of the absorbent article, parallel to a feed direction; the process according to this invention is therefore implemented in the so-called "machine direction".

In the preferred embodiment illustrated, the web 2 is preferably the web which will constitute the "topsheet" of the semi-finished items 1 and of the corresponding absorbent articles.

With reference in particular to FIG. 1 and from 6 to 9, together with the web 2, the generic absorbent pads 5 are also illustrated, by the dashed lines. As illustrated, the pads 5 have, along the direction D, a first end at the front portion 3a, 4a of the respective stretch 3, 4 of web 2, and a second end at the rear portion 3b, 4b of the respective stretch 3, 4 of web 2.

For greater clarity, the ends of the absorbent pads 5 positioned at the front end portions 3a, 4a of the stretches 3, 4 are shown tapered relative to the ends of the absorbent pads 5 positioned at the rear end portions 3b, 4b of the stretches 3, 4.

In one embodiment, the pads 5 are effectively already associated, in known manner, with the web 2; in alternative embodiments, the pads 5 are associated with the web 2 in successive steps, known and not described, and the web comprises only the above-mentioned first and second stretches 3, 4.

In the process according to this invention, the first stretches (sections) 3 of the web 2 are oriented, in the web 2 itself, in such a way that each first stretch has the rear end portion 3b, corresponding to the rear end portion of the corresponding first layer, upstream of the front end portion 3a, corresponding to the front end portion of the same first layer, in the feed direction V of the web 2.

In the process according to this invention, the second stretches (sections) 4 of the web 2 are oriented, in the web 2 itself, in such a way that each second stretch has the front end portion 4a, corresponding to the front end portion of the corresponding first layer, upstream of the rear end portion 4b, corresponding to the rear end portion of the same first layer, in the feed direction V of the web 2.

In the preferred embodiment illustrated by way of an example, the stretches 3 and 4 are provided in an alternating succession in the web 2, that is, a stretch 3 is followed by a stretch 4.

In alternative embodiments not illustrated, the succession of the stretches 3 and 4 in the web 2 is different, notwithstanding that the web 2 comprises stretches 3 and 4 oriented as described.

Figure 2:
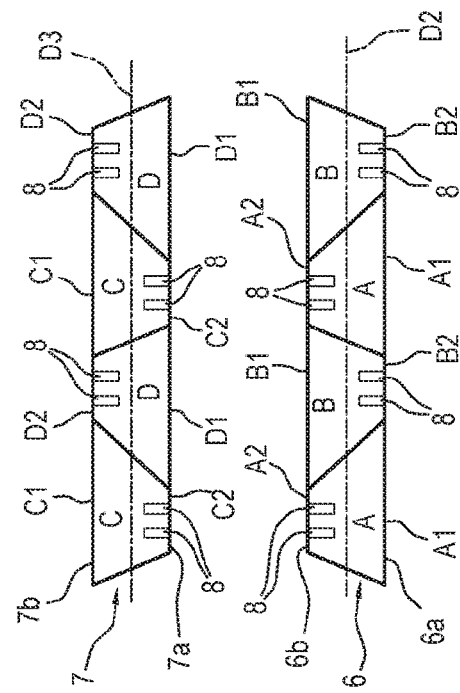

With reference in particular to FIG. 2, the process comprises a step for feeding a second web 6 designed for forming the above-mentioned first panel, for example rear panel, of the finished nappy.

The process comprises a step for feeding a third web 7 designed for forming the above-mentioned second panel, for example rear panel, of the finished nappy.

The webs 6 and 7 each have a respective main direction of extension D2, D3 and a first and a second side edge 6a, 7a, 6b, 7b substantially straight and extending parallel to the main direction of extension D2, D3.

The process comprises a step of cutting the second web 6 in a succession of a first piece A and a second piece B, each forming, as will be described in more detail below, a first panel, for example rear panel, of the finished nappy.

The process comprises a step of cutting the third web 7 in a succession of a third piece C and a fourth piece D, each forming, as will be described in more detail below, a second panel, for example rear panel, of the finished nappy.

The pieces A, B, C, D each have a first end A1, B1, C1, D1 connecting with the first layer and a second end A2, B2, C2, D2 opposite the first end A1, B1, C1, D1, designed to engage, in use, with a corresponding panel, as will be described in more detail below.

As illustrated, the pieces A have the first end A1 located on the edge 6a and the second end A2 located on the edge 6b.

More specifically, the first end A1 is defined by the edge 6a and the second end A2 is defined by the edge 6b.

The pieces B have the first end B1 located on the edge 6b and the second end B2 located on the edge 6a.

More specifically, the first end B1 is defined by the edge 6b and the second end B2 is defined by the edge 6a.

The pieces C have the first end C1 located on the edge 7b and the second end C2 located on the edge 7a.

More specifically, the first end C1 is defined by the edge 7b and the second end C2 is defined by the edge 7a.

The pieces D have the first end D1 located on the edge 7a and the second end D2 located on the edge 7b.

More specifically, the first end D1 is defined by the edge 7a and the second end C2 is defined by the edge 7b.

In the preferred embodiment given by way of an example, wherein the pieces A, B, C, D, will constitute the rear panels of the nappy, the process comprises a step of applying on the second web 6 and on the third web 7 a system 8, of substantially known type and not further described, for closing the absorbent sanitary article when in use.

The closing systems 8 are applied on the second web 6 and on the third web 7 at the second ends A2, B2, C2, D2 of the pieces A, B, C, D.

Looking in more detail at the step of cutting the webs 6 and 7, it should be noted that the cutting step comprises a step of making a plurality of cuts which are oblique relative to the main direction of extension D2 of the second web 6 and a step of making a plurality of cuts which are oblique relative to the main direction of extension D3 of the third web 7.

As illustrated, the cuts in the second web 6 are made in such a way that the second pieces F are shaped like the first pieces A and rotated, in the plane of the second web 6, by 180° relative to the first pieces A.

Preferably, the pieces A and B are in the form of a trapezium, for example scalene, with the bases defined by the edges 6a, 6b of the web 6.

As illustrated, the larger base of each piece A, B defines the respective above-mentioned first end A1, B1 for connecting the same piece to the web 2 as will be described in more detail below.

As illustrated, the cuts in the third web 7 are made in such a way that the third pieces C are shaped in such a way as to be symmetrical with the first pieces E relative to a straight line passing through the base of the piece A defined by the edge 6b of the web 6.

In other words, the pieces C are specular to the pieces A with respect to a straight line parallel to the base of the piece A defined by the edge 6b of the web 6.

The cuts in the third web 7 are also made in such a way that the fourth pieces D are shaped like the third pieces C and rotated, in the plane of the third web 7, by 180° relative to the third pieces C.

Preferably, the pieces C and D are in the form of a trapezium, for example scalene, with the bases defined by the edges 7a, 7b of the web 7.

As illustrated, the larger base of each piece C, D defines the respective above-mentioned first end C1, D1 for connecting the same piece C, D to the web 2 as will be described in more detail below.

With reference in particular to FIGS. 6 and 7, it should be noticed that the process according to this invention comprises a step of applying the pieces A, B, C, D to the first web 2.

The step of applying the pieces A, B, C, D to the first web 2 comprises a step of positioning a first piece A on a first stretch 3 of the first web 2.

The piece A is positioned at the rear end portion 3b of the stretch 3.

The piece A is preferably positioned on the web 2 with the end A2 facing towards the centre of the web 2, that is, the piece A is positioned on the web 2 in a folded configuration of the corresponding first rear panel.

The step of applying the pieces A, B, C, D to the first web 2 comprises a step of positioning a second piece B on a second stretch 4 of the first web 2.

The piece B is positioned at the rear end portion 4b of the stretch 4.

The piece B is preferably positioned on the web 2 with the end B2 facing towards the centre of the web 2, that is, the piece B is positioned on the web 2 in a folded configuration of the corresponding first rear panel.

The piece B is positioned on the web 2 on the side opposite the first piece A relative to the web 2.

In the preferred embodiment illustrated, once the piece A has been applied on a stretch 3 of the web 2, a piece B is applied on the stretch 4 after the stretch 3 in the feed direction V of the web 2.

The step of applying the pieces A, B, C, D to the first web 2 comprises a step of positioning a third piece C on a first stretch 3 of the first web 2.

The piece C is positioned at the rear end portion 3b of the stretch 3.

The piece C is preferably positioned on the web 2 with the end C2 facing towards the centre of the web 2, that is, the piece C is positioned on the web 2 in a folded configuration of the corresponding first rear panel.

The piece C is positioned on the web 2 on the side opposite the first piece A relative to the web 2.

The step of applying the pieces A, B, C, D to the first web 2 comprises a step of positioning a fourth piece D on a second stretch 4 of the first web 2.

The piece D is positioned at the rear end portion 4b of the stretch 4.

The piece D is preferably positioned on the web 2 with the end D2 facing towards the centre of the web 2, that is, the piece D is positioned on the web 2 in a folded configuration of the corresponding first rear panel.

The piece D is positioned on the web 2 on the side opposite the second and third piece B, C relative to the web 2, that is, it is positioned on the same side of piece A.

In the preferred embodiment illustrated, once the piece C has been applied on a stretch 3 of the web 2, a piece D is applied on the stretch 4 after the stretch 3 in the feed direction V of the web 2.

Advantageously, the special shape of the web 2, with the first and second stretches 3, 4 oriented in the opposite direction with reference to the feed direction V of the web 2, allows the application of the pieces A, B, C, D cut as described, that is to say, without waste from the respective webs 6, 7 and with any preferred embodiment, without having to rotate any of the pieces A, B, C, D.

Advantageously, the first pieces A and the third pieces C are applied on the web 2 in such a way that the second end A2 of the first piece A is facing the second end C2 of the third piece C.

Advantageously, the second pieces A and the fourth pieces C are applied on the web 2 in such a way that the second end B2 of the second piece B is facing the second end D2 of the fourth piece D.

Figures 4, 5:
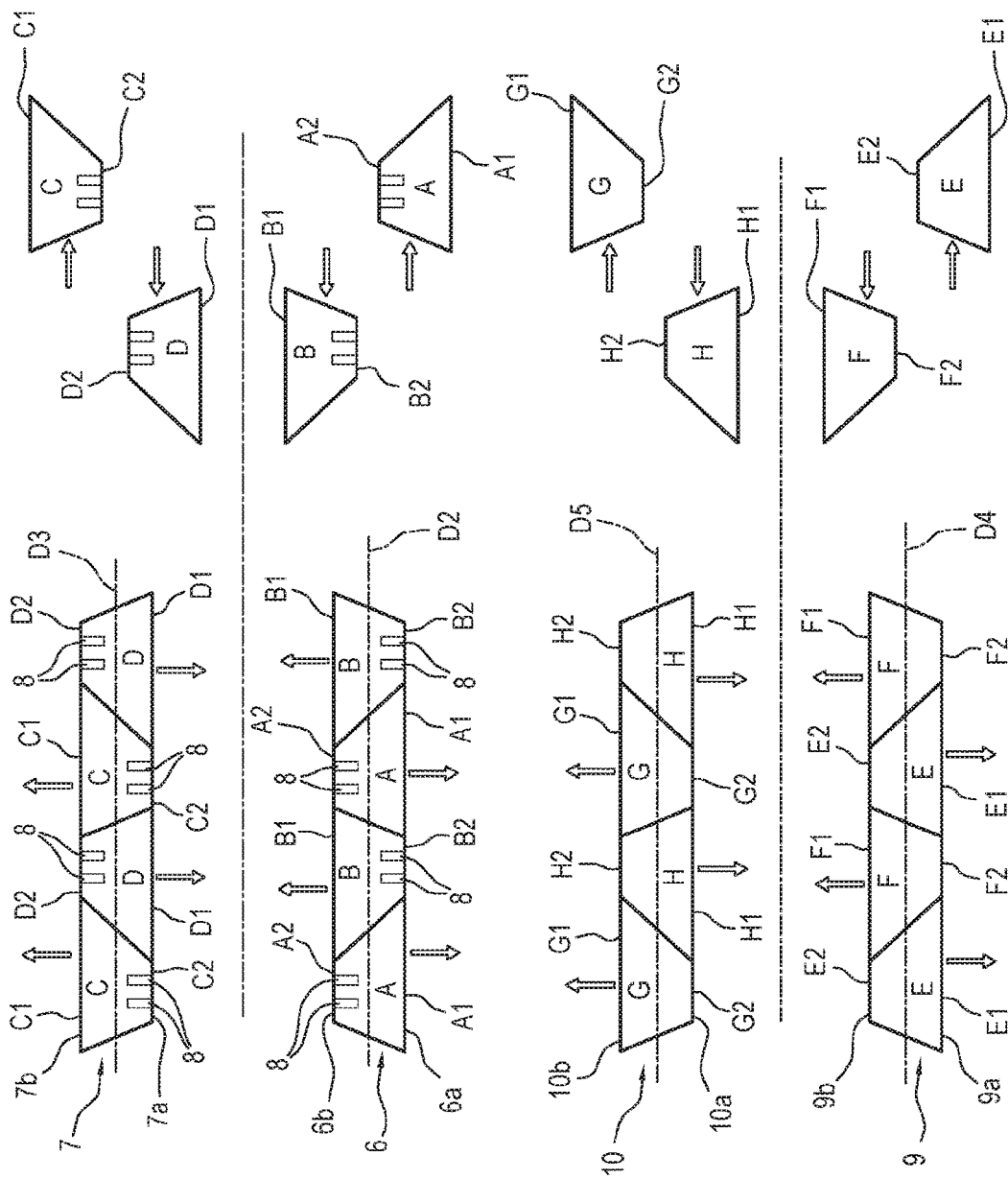

With reference in particular to FIG. 4, looking in more detail at the movement of the pieces A, B, C, D, it should be noted that the process comprises a step of translating the second pieces B relative to the first pieces A in a direction parallel to the main direction of extension D2 of the web 6 to allow the positioning of the pieces A and B, respectively, on a first and a second stretch 3, 4 of the web 2.

The process comprises a step of translating the second pieces B relative to the first pieces A along a direction transversal to the main direction of extension D2 of the web 6 for allowing the positioning of the pieces A and B on opposite sides of the web 2.

The process comprises a step of translating the fourth pieces D relative to the third pieces C along a direction parallel to the main direction of extension D3 of the web 7 for allowing the positioning of the pieces C and D, respectively, on a first and a second stretch 3, 4 of the web 2.

The process comprises a step of translating the fourth pieces D relative to the third pieces C along a direction transversal to the main direction of extension D3 of the web 7 for allowing the positioning of the pieces C and D on opposite sides of the web 2.

The process according to this invention comprises a succession of substantially similar steps for also preparing on the web 2 the above-mentioned front panels of the absorbent sanitary article.

Figure 3:
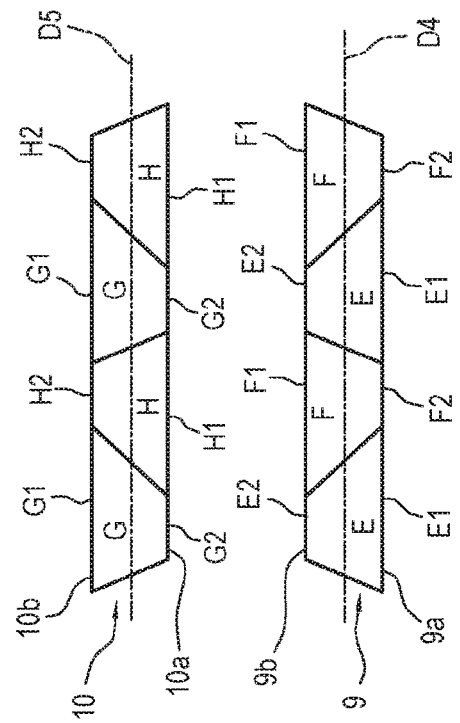

With reference in particular to FIG. 3, the process comprises a step for feeding a fourth web 9 designed for forming the above-mentioned first front panel.

The process comprises a step for feeding a fifth web 10 designed for forming the above-mentioned second front panel of the finished nappy.

The webs 9 and 10 each have a respective main direction of extension D4, D5 and a first and a second side edge 9a, 10a, 9b, 10b substantially straight and extending parallel to the main direction of extension D4, D5.

The process comprises a step of cutting the fourth web 9 in a succession of a fifth piece E and a sixth piece F, each forming, as will be described in more detail below, a first front panel of the finished nappy.

The process comprises a step of cutting the fifth web 10 in a succession of a seventh piece G and an eighth piece H, each forming, as will be described in more detail below, an above-mentioned second front panel of the finished nappy.

The pieces E, F, G, H each have a first end E1, F1, G1, H1 connecting with the first layer and a second end E2, F2, G2, H2 opposite the first end E1, F1, G1, H1, designed to engage, in use, with a corresponding rear panel, as will be described in more detail below.

As illustrated, the pieces E have the first end E1 located on the edge 9*a* and the second end E2 located on the edge 9*b*.

More specifically, the first end E1 is defined by the edge 9*a* and the second end A2 is defined by the edge 9*b*.

The pieces D have the first end F1 located on the edge 9*b* and the second end F2 located on the edge 9*a*.

More specifically, the first end F1 is defined by the edge 9*b* and the second end F2 is defined by the edge 9*a*.

The pieces G have the first end G1 located on the edge 10*b* and the second end G2 located on the edge 10*a*.

More specifically, the first end G1 is defined by the edge 10*b* and the second end G2 is defined by the edge 10*a*.

The pieces H have the first end H1 located on the edge 10*a* and the second end H2 located on the edge 10*b*.

More specifically, the first end H1 is defined by the edge 9*b* and the second end F2 is defined by the edge 9*a*.

Looking in more detail at the step of cutting the webs 9 and 10, it should be noted that the cutting step comprises a step of making a plurality of cuts which are oblique relative to the main direction of extension D4 of the fourth web 9 and a step of making a plurality of cuts which are oblique relative to the main direction of extension D5 of the fifth web 10.

As illustrated, the cuts in the fourth web 9 are made in such a way that the sixth pieces F are shaped like the fifth pieces E and rotated, in the plane of the fourth web 9, by 180° relative to the fifth pieces E.

Preferably, the pieces E and F are in the form of a trapezium, for example scalene, with the bases defined by the edges 9*a*, 9*b* of the web 9.

As illustrated, the larger base of each piece E, F defines the respective above-mentioned first end E1, F1 for connecting the same piece to the web 2 as will be described in more detail below.

As illustrated, the cuts in the fifth web 10 are made in such a way that the seventh pieces G are shaped in such a way as to be symmetrical with the fifth pieces E relative to a straight line passing through the base of the piece E defined by the edge 9*b* of the web 9.

In other words, the pieces G are specular to the pieces A with respect to a straight line parallel to the base of the piece E defined by the edge 9*b* of the web 9.

The cuts in the fifth web 10 are also made in such a way that the eighth pieces H are shaped like the seventh pieces G, and rotated, in the plane of the fifth web 10, by 180° relative to the seventh pieces G.

Preferably, the pieces G and H are in the form of a trapezium, for example scalene, with the bases defined by the edges 10*a*, 10*b* of the web 10.

As illustrated, the larger base of each piece G, H defines the respective above-mentioned first end G1, H1 for connecting the same piece G, H to the web 2 as will be described in more detail below.

With reference in particular to FIGS. 8 and 9, it should be noticed that the process according to this invention comprises a step of applying the pieces E, F, G, H to the first web 2.

The step of applying the pieces E, F, G, H to the first web 2 comprises a step of positioning a fifth piece E on a second stretch 4 of the first web 2.

The piece E is positioned at the rear end portion 4*a* of the stretch 4.

The piece E is preferably positioned on the web 2 with the end E2 facing towards the centre of the web 2, that is, the piece E is positioned on the web 2 in a folded configuration of the corresponding first front panel.

The step of applying the pieces E, F, G, H to the first web 2 comprises a step of positioning a sixth piece E on a first stretch 3 of the first web 2.

The piece F is positioned at the rear end portion 3*a* of the stretch 3.

The piece F is preferably positioned on the web 2 with the end F2 facing towards the centre of the web 2, that is, the piece F is positioned on the web 2 in a folded configuration of the corresponding first front panel.

The piece F is positioned on the web 2 on the side opposite the first piece E relative to the web 2.

In the preferred embodiment illustrated, once the piece E has been applied on a stretch 4 of the web 2, a piece F is applied on the stretch 3 after the stretch 4 in the feed direction V of the web 2.

The step of applying the pieces E, F, G, H to the first web 2 comprises a step of positioning a seventh piece G on a second stretch 4 of the first web 2.

The piece G is positioned at the rear end portion 4*a* of the stretch 4.

The piece G is preferably positioned on the web 2 with the end G2 facing towards the centre of the web 2, that is, the piece G is positioned on the web 2 in a folded configuration of the corresponding second front panel.

The piece G is positioned on the web 2 on the side opposite the first piece E relative to the web 2.

The step of applying the pieces E, F, G, H to the first web 2 comprises a step of positioning an eighth piece H on a first stretch 3 of the first web 2.

The piece H is positioned at the rear end portion 3*a* of the stretch 3.

The piece H is preferably positioned on the web 2 with the end H2 facing towards the centre of the web 2, that is, the piece H is positioned on the web 2 in a folded configuration of the corresponding first rear panel.

The piece H is positioned on the web 2 on the side opposite the sixth and seventh piece F, G relative to the web 2, that is, it is positioned on the same side of piece E.

In the preferred embodiment illustrated, once the piece G has been applied on a stretch 4 of the web 2, a piece H is applied on the stretch 3 after the stretch 4 in the feed direction V of the web 2.

Advantageously, the special shape of the web 2, with the first and second stretches 3, 4 oriented in the opposite direction with reference to the feed direction V of the web 2, allows the application of the pieces E, F, G, H cut as described, that is to say, without waste from the respective webs 9, 10 and with any preferred embodiment, without having to rotate any of the pieces E, F, G, H.

Advantageously, the fifth pieces A and the seventh pieces C are applied on the web 2 in such a way that the second end E2 of the fifth piece E is facing the second end G2 of the seventh piece G.

Advantageously, the sixth pieces A and the eighth pieces H are applied on the web 2 in such a way that the second end F2 of the sixth piece F is facing the second end H2 of the eighth piece H.

With reference in particular to FIG. 5, looking in more detail at the movement of the pieces E, F, G, H, it should be noted that the process comprises a step of translating the sixth pieces F relative to the fifth pieces E in a direction parallel to the main direction of extension D4 of the web 9 to allow the positioning of the pieces G and H, respectively, on a first and a second stretch 4, 3 of the web 2.

The process comprises a step of translating the sixth pieces F relative to the fifth pieces E along a direction transversal to the main direction of extension D4 of the web 9 for allowing the positioning of the pieces E and F on opposite sides of the web 2.

The process comprises a step of translating the eighth pieces H relative to the seventh pieces G along a direction parallel to the main direction of extension D5 of the web 10 for allowing the positioning of the pieces G and H, respectively, on a second and a first stretch 4, 3 of the web 2.

The process comprises a step of translating the eighth pieces H relative to the seventh pieces G along a direction transversal to the main direction of extension D5 of the web 10 for allowing the positioning of the pieces G and H on opposite sides of the web 2.

Once the pieces A, B, C, D, E, F, G, H are positioned on the web 2 as described above, the process comprises a step of folding the first ends A1, B1, C1, D1, E1, F1, G1, H1 on the opposite side of the first web 2 relative to the second ends A2, B2, C2, D2, E2, F2, G2, H2.

More specifically, for implementing the folding step, the pieces A, B, C, D, E, F, G, H are positioned on the web 2 in such a way that the first ends A1, B1, C1, D1, E1, F1, G1, H1 extend cantilever-style from the first web 2 at the end of the respective applying step.

Once the ends have been folded, the process comprises a step of applying at least a sixth web, not illustrated, to the first web 2 and designed to form a second layer of the above-mentioned main body, for example, the "backsheet".

The ends A1, B1, C1, D1, E1, F1, G1, H1 of the pieces A, B, C, D, E, F, G, H thus remain blocked between the first web 2 and the sixth web, thus guaranteeing the joining of the pieces and the corresponding panels to the main body of the corresponding nappy.

The forming process comprises further known steps not described to achieve the production of a plurality of absorbent sanitary articles starting from the semi-finished item illustrated in FIG. 9.

The process as described brings important advantages; it allows the application of so-called asymmetrical panels without waste of material, that is, it is a "zero waste" type process, completely avoiding the critical aspects due, in prior art processes, to the rotation of the panels. The use of different webs panels between front and rear panels allows the type of material used to be differentiated on the basis of the needs, in particular to limit the costs of the finished product whilst granting it a good wearability as it can adopt, for example, elastic material only where it is needed.

The invention claimed is:

1. A process for forming an absorbent sanitary article, wherein the absorbent sanitary article comprises:
   a main body having a main direction of extension and including at least a first layer having a front end portion and a rear end portion:
   at least a first side panel and a second side panel connected to at least the first layer,
   the process comprising:
   a step of feeding in a feed direction a first web comprising alternating first and second sections, each defining at least the first layer of the main body and having a front end portion and a rear end portion corresponding to the front end portion and to the rear end portion of the corresponding main body of the absorbent sanitary article;
   a step of feeding a second web configured for forming the first side panel;
   a step of feeding a third web configured for forming the second side panel;
   a step of cutting the second web in a succession of a first piece and a second piece, the first piece and second piece defining the first side panel of the first section and the second section respectively;
   a step of cutting the third web in a succession of a third piece and a fourth piece, the third piece and fourth piece defining the second side panel of the first section and the second section respectively;
   the first, second, third and fourth pieces each having a first end connecting with the first layer and a second end opposite the first end,
   a step of applying the first, second, third and fourth pieces to the first web,
   a step of providing the first and second sections in the first web in such a way that
      each first section has the rear end portion upstream of the front end portion along the feed direction and
      each second section has the front end portion upstream of the rear end portion along the feed direction.

2. The process according to claim 1, wherein the step of applying the first, second, third and fourth pieces comprises:
   a step of positioning the first piece on the first section of the first web;
   a step of positioning the second piece on the second section of the first web on an opposite side of the first piece relative to the first web;
   a step of positioning the third piece on the first section of the first web on the opposite side of the first piece relative to the first web;
   a step of positioning the fourth piece on the second section of the first web on an opposite side of the second and third piece relative to the first web.

3. The process according to claim 1, wherein the first piece and the third piece are applied on the first web in such a way that the second end of the first piece is facing the second end of the third piece.

4. The process according to claim 1, wherein the second piece and the fourth piece are applied on the first web in such a way that the second end of the second piece is facing the second end of the third piece.

5. The process according to claim 1, comprising a step of folding the first ends of the first, second, third and fourth pieces on an opposite side of the first web relative to the second end of the first, second, third and fourth pieces, the first ends extending in a cantilever manner from the first web at the end of the applying step.

6. The process according to claim 1, wherein the step of applying the first, second, third and fourth pieces comprises a step of translating the second piece relative to the first piece along a direction parallel to a main direction of extension of the second web.

7. The process according to claim 1, wherein the step of applying the first, second, third and fourth pieces comprises a step of translating the second piece relative to the first piece along a direction transversal to a main direction of extension of the second web.

8. The process according to claim 1, wherein the step of applying the first, second, third and fourth pieces comprises a step of translating the fourth piece relative to the third piece along a direction parallel to a main direction of extension of the third web.

9. The process according to claim 1, wherein the step of applying the first, second, third and fourth pieces comprises a step of translating the fourth piece relative to the third piece along a direction transversal to a main direction of extension of the third web.

10. The process according to claim 1, comprising a step of applying at least a fourth web to the first web to define a second layer of the main body, the first ends of the first, second, third and fourth pieces remaining blocked between the first web and the fourth web.

11. The process according to claim 1, wherein the first, second, third and fourth pieces are positioned on the respective first or second sections of the first web at least at the rear end portions.

12. The process according to claim 1, comprising a step of applying on the second and third web a closing system for closing the absorbent sanitary article, the closing system being applied on the second and third web at the second end of the first, second, third and fourth pieces.

13. The process according to claim 1, wherein the first, second, third and fourth pieces are positioned on the respective first or second sections of the first web at least at the front end portions.

14. The process according to claim 1, wherein the first, second, third and fourth pieces are positioned on the respective first or second sections of the first web at the rear end portions, the process comprising:
   a step of feeding a fourth web and a fifth web configured respectively for forming a third side panel and a fourth side panel,
   a step of cutting the fourth web in a succession of fifth and sixth pieces forming the third side panel of the second section and the first section respectively;
   a step of cutting the fifth web in a succession of a seventh and eighth pieces forming the fourth side panel of the second section and the first section respectively;
   the fifth, sixth, seventh and eighth pieces each having a first end connecting with the first layer and a second end opposite the first end,
   a step of applying the fifth, sixth, seventh and eighth pieces to the first web at front end portions,
   the step of applying the fifth, sixth, seventh and eighth pieces comprising a step of positioning the fifth piece on the second section of the first web;
   a step of positioning the sixth piece on the first section of the first web on an opposite side of the fifth piece relative to the first web;
   a step of positioning the seventh piece on the second section of the first web on the opposite side of the fifth piece relative to the first web;
   a step of positioning the eighth piece on the first section of the first web on an opposite side of the sixth and seventh pieces relative to the first web, the first and third pieces configured to engage, in use, respectively, with the eighth and sixth pieces and the second and fourth pieces configured to engage, in use, respectively, with the seventh and fifth pieces.

15. The process according to claim 14, wherein the step of applying the fifth, sixth, seventh and eighth pieces comprises a step of translating the sixth piece relative to the fifth piece in a direction parallel to a main direction of extension of the fourth web.

16. The process according to claim 14, wherein the step of applying the fifth, sixth, seventh and eighth pieces comprises a step of translating the sixth piece relative to the fifth piece in a direction parallel to a main direction of extension of the fourth web.

17. The process according to claim 14, wherein the step of applying the fifth, sixth, seventh and eighth pieces comprises a step of translating the eighth piece relative to the seventh piece in a direction parallel to a main direction of extension of the fifth web.

18. The process according to claim 14, wherein the step of applying the fifth, sixth, seventh and eighth pieces comprises a step of translating the eighth piece relative to the seventh piece in a direction transversal to a main direction of extension of the fifth web.

19. The process according to claim 14, wherein
   the step of cutting the fourth web comprises a step of making a plurality of cuts which are oblique relative to a main direction of extension of the fourth web and
   the step of cutting the fifth web comprises a step of making a plurality of cuts which are oblique relative to a main direction of extension of the fifth web,
   the cuts in the fourth web and the cuts in the fifth web being provided in such a way that the sixth pieces are shaped like the fifth pieces and rotated, in a plane of the fourth web, by 180° relative to the fifth pieces, the eighth pieces are shaped like the seventh pieces and rotated, in a plane of the fifth web, by 180° relative to the seventh pieces and the seventh pieces are shaped in such a way as to be symmetrical with the fifth pieces.

20. The process according to claim 1, wherein
   the step of cutting the second web comprises a step of making a plurality of cuts which are oblique relative to a main direction of extension of the second web and the step of cutting the third web comprises a step of making a plurality of cuts which are oblique relative to a main direction of extension of the third web,
   the cuts in the second web and the cuts in the third web being provided in such a way that the second pieces are shaped like the first pieces and rotated, in a plane of the second web, by 180° relative to the first pieces, the fourth pieces are shaped like the third pieces and rotated, in a plane of the third web, by 180° relative to the third pieces and the third pieces are shaped in such a way as to be symmetrical with the first pieces.

* * * * *